(12) United States Patent
Depeursinge

(10) Patent No.: US 6,625,518 B2
(45) Date of Patent: Sep. 23, 2003

(54) METHOD SUPPORTING ADMINISTRATION OF A PRESCRIBED DRUG AND IMPLEMENTING SAID METHOD

(75) Inventor: Yves Depeursinge, Servion (CH)

(73) Assignee: Csem Centre Suisse d'Electronique et de Microtechnique SA (CH)

( * ) Notice: Subject to any disclaimer, the term of this patent is extended or adjusted under 35 U.S.C. 154(b) by 0 days.

(21) Appl. No.: 10/253,535

(22) Filed: Sep. 25, 2002

(65) Prior Publication Data

US 2003/0023345 A1 Jan. 30, 2003

Related U.S. Application Data

(63) Continuation of application No. 09/598,752, filed on Jun. 22, 2000, now abandoned.

(51) Int. Cl.$^7$ .............................................. G06F 17/00
(52) U.S. Cl. .......................... 700/242; 700/237; 221/2; 221/15
(58) Field of Search ................................ 700/231, 237, 700/242, 243; 368/10; 221/2, 3, 15

(56) References Cited

U.S. PATENT DOCUMENTS

| | | | |
|---|---|---|---|
| 4,473,884 A | | 9/1984 | Behl |
| 4,572,403 A | * | 2/1986 | Benaroya ........................ 221/3 |
| 4,617,557 A | | 10/1986 | Gordon |
| 4,682,299 A | | 7/1987 | McIntosh et al. ............ 364/569 |
| 4,785,969 A | | 11/1988 | McLaughlin |
| 4,926,572 A | * | 5/1990 | Holmes ......................... 40/448 |
| 4,971,221 A | * | 11/1990 | Urquhart et al. ................ 221/2 |
| 5,099,463 A | | 3/1992 | Lloyd et al. |
| 5,148,944 A | | 9/1992 | Kaufman et al. ............ 221/131 |
| 5,176,285 A | | 1/1993 | Shaw |
| 5,181,189 A | | 1/1993 | Hafner |
| 5,200,891 A | | 4/1993 | Kehr et al. |
| 5,289,157 A | * | 2/1994 | Rudick et al. .......... 340/309.15 |
| 5,392,952 A | | 2/1995 | Bowden |
| 5,408,443 A | | 4/1995 | Weinberger |
| 5,412,372 A | | 5/1995 | Parhurst et al. |
| 5,522,525 A | | 6/1996 | McLaughlin et al. |
| 5,805,051 A | | 9/1998 | Herrmann et al. |
| 5,850,937 A | | 12/1998 | Rauche |
| 5,852,590 A | | 12/1998 | de la Huerga ................. 368/10 |
| 5,915,558 A | * | 6/1999 | Girvetz ........................ 206/534 |

(List continued on next page.)

FOREIGN PATENT DOCUMENTS

| | | |
|---|---|---|
| DE | 195 44 294 A | 6/1997 |
| DE | 195 44 294 A1 | 6/1997 |
| EP | 0 827 733 A1 | 3/1998 |
| FR | 2 750 857 | 1/1998 |
| WO | WO 9925307 | 5/1999 |

*Primary Examiner*—Khoi H. Tran
(74) *Attorney, Agent, or Firm*—Parkhurst & Wendel, L.L.P.

(57) ABSTRACT

A support procedure for administering prescription drugs which does not require patient action while avoiding erroneous patient manipulation in order to carry out error-free home treatment, wherein the procedure includes the following steps:

STEP 1
    prior preparation of one or more drug doses,
    programming and storing identifying parameters in a computer (1), STEP 2
    individual insertion of each dose in a pack (2) which is subsequently sealed, and
    entering the parameters on an arbitrary storage substrate (3) applied to the pack (2), STEP III:
    integrating the pack into a dispenser (4) of which the operation is programmable and which includes a means for reading the parameters.

11 Claims, 2 Drawing Sheets

U.S. PATENT DOCUMENTS

| | | | |
|---|---|---|---|
| 5,954,225 A | * | 9/1999 | Powe .............................. 221/2 |
| 6,004,020 A | | 12/1999 | Bartur |
| 6,032,085 A | | 2/2000 | Laurent et al. |
| 6,048,087 A | | 4/2000 | Laurent et al. |
| 6,082,544 A | * | 7/2000 | Romick ...................... 206/531 |
| 6,138,865 A | | 10/2000 | Gilmore |
| 6,169,707 B1 | | 1/2001 | Newland |
| 6,259,654 B1 | | 7/2001 | DeLaHuerga |
| 6,281,798 B1 | * | 8/2001 | Laurent et al. .......... 340/573.1 |

\* cited by examiner

METHOD SUPPORTING ADMINISTRATION OF A PRESCRIBED DRUG AND IMPLEMENTING SAID METHOD

This is a Continuation of application Ser. No. 09/598,752 filed Jun. 22, 2000, now abandoned.

FIELD OF THE INVENTION

The present invention relates to a support method for administrating medically prescribed drugs without patient action, thereby averting patient mishandling in order to carry out home patient care, without danger of mistakes.

BACKGROUND OF THE INVENTION

In particular for the aged, there are presently surveillance networks with central sites that call qualified personnel or a family member when an alarm is triggered by the aged person from home. Such an alarm is emitted when the aged person, wearing a case suspended from the neck or the wrist, and actuates the alarm via a button on its case.

By a well known manner, the case's signal generator radios the central site which in turn transmits the signal to a base station.

Furthermore, such a network allows remote monitoring of various patient parameters such as temperature, heartbeat, etc.

In this regard, applicant discloses in its patent application FR/97 05547 a device for monitoring a person's activities, and able to detect a fall so as to provide help. All these systems provide tangible help to the aged, the handicapped, or convalescents. However, they would fruitfully be complemented by a system assisting such people in taking drugs in the right doses and at the right time, as prescribed by their physicians. Indeed, the invention's method and device intend to reduce the possibilities of mistakes when taking such drugs and also to avert mistakes in preparing the drug doses.

SUMMARY OF THE INVENTION

For that purpose the present invention relates to a method to help administrator prescription drugs without patient action and avoids patient errors so as to allow error-free home care. The method includes the following steps:

STEP I
  prior preparation of one or more drug doses, prescribed by a physician, at a pharmacy;
  programming and storing in a computer patient identification parameters (name, address, social security number) and the preparation corresponding to the prescribed drug(s) (drug name(s), dosage(s), ingestion time(s)).

STEP II
  inserting the dosed drugs in a pack which is sealed thereafter,
  transcribing the parameters onto a storage substrate integrated into the pack before transfer to the patient or medical personnel.

STEP III:
  integrating the pack into a programmable dispenser which can be either manually, or automatically locked and initially is unlocked in order to feed the drug doses as a function of parameters stored in memory in the pack's storage substrate and which are identified by the dispenser using an arbitrary read means when the parameters are called into play.

The invention furthermore relates to a device for implementing the method.

The present invention also concerns features which are elucidated in the following description and must be considered singly or in any conceivable technical combination.

This description is provided in an illustrative, but non-limiting manner, and elucidates the implementation of the invention in relation to the attached drawings.

DETAILED DESCRIPTION OF THE INVENTION

Figure 1:
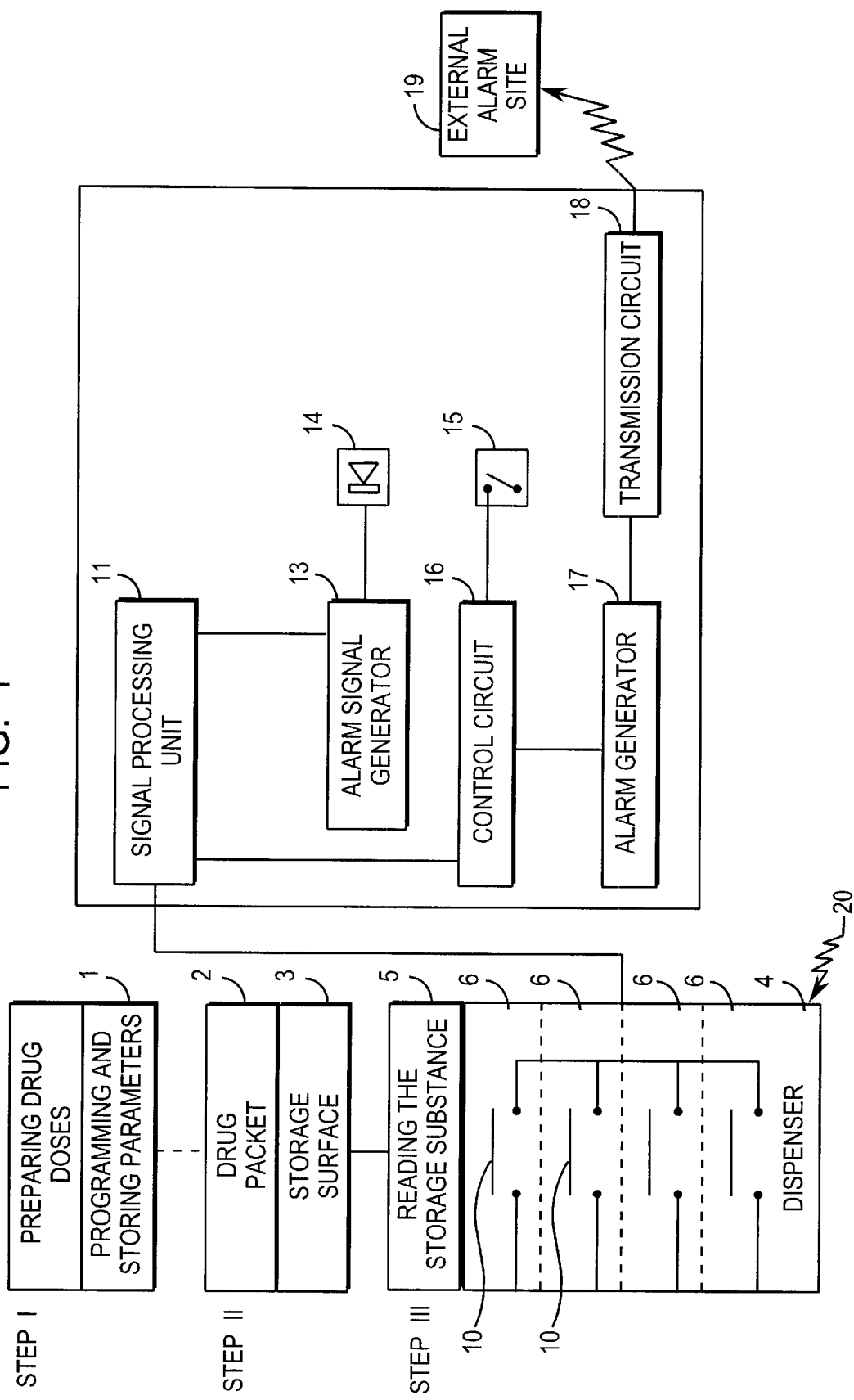
FIG. 1 is a summary diagram of a device of the invention assisting drug ingestion.

The method assisting in prescription-drug administration is plotted in FIG. 1.

The invention also concerns a device implementing the above method and includes (FIG. 2) the following components:

a pack 2 wherein a pharmacist places at least one drug dose which was previously prepared by the pharmacist in the pharmacy, the pack 2 thereupon being hermetically sealed and ultimately made available to the patient or some medical personnel, a storage substrate 3 joined to the pack element 2 and containing all patient identifying parameters, specific name, address, social security number etc., and the preparation of the prescribed drug: drug name(s), drug doses, time(s) of administration etc., an initially locked programmed dispenser 4 which can be manually or automatically unlocked to dispense one or more drug doses as a function of the parameters stored in the (pack's 2) storage.

means 5 identifying and reading the parameters and joined to the dispenser 4 and activated when the dispenser is combined with the pack 2 for the drug doses to be administered.

Figure 2:
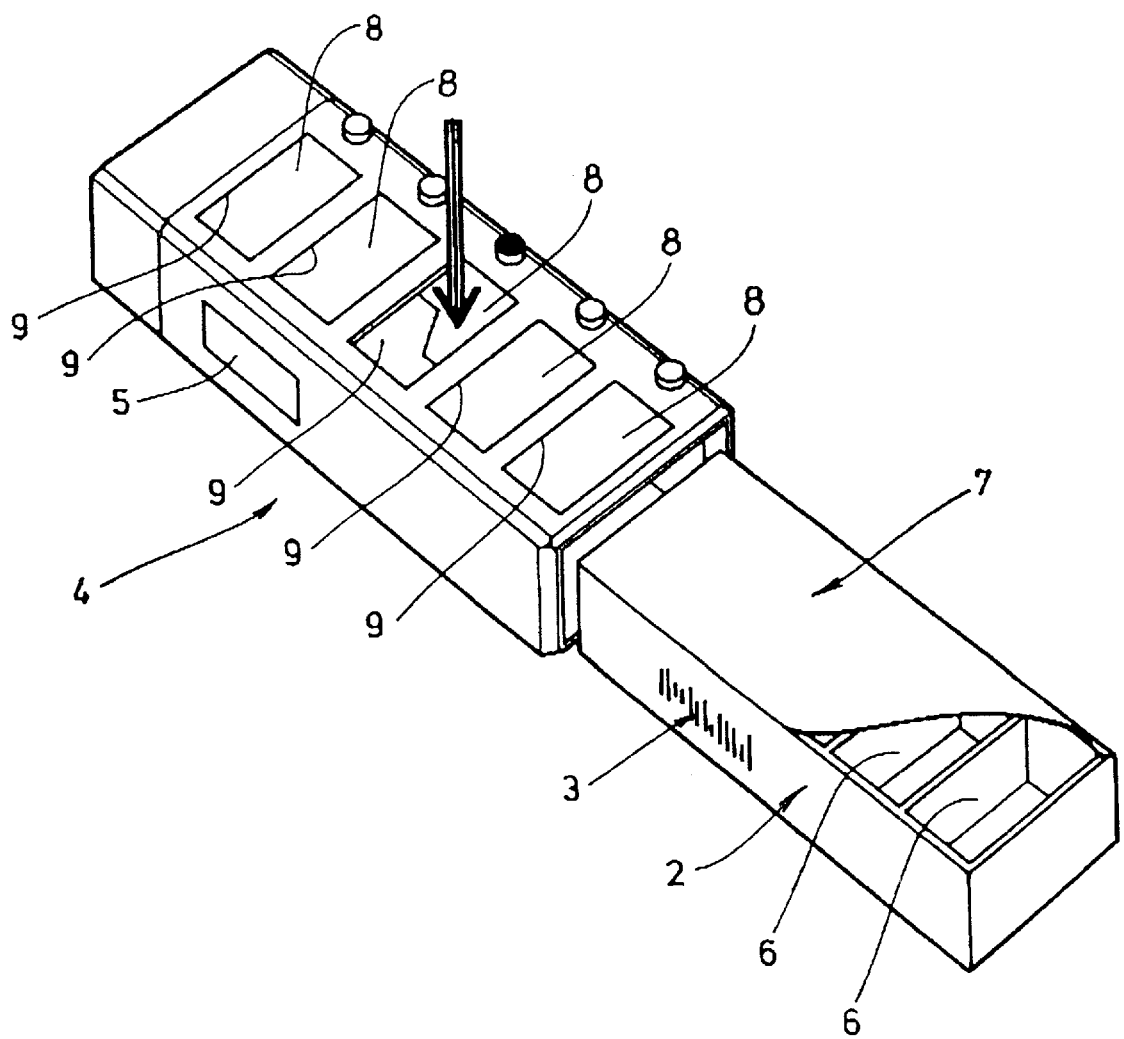
FIG. 2 is an exploded perspective of a drug pack and of an associated dispenser.

In one illustrative, and non-limiting embodiment, the pack 2 and dispenser 4 shown in FIG. 2 are particularly designed to contain drug doses in tablet form.

Obviously, such components may be modified to hold drugs in liquid, powder, or other forms.

In the embodiment, accordingly, the pack 2 consists of a container divided into a plurality of compartments 6 each of which holds the previously loaded tablet(s) corresponding to a given drug dose to be ingested by the patient at a given time and at given time intervals.

The container constituting the pack 2 may be a compartmentalized drawer of an overall parallelipipedic shape.

Preferably, the container is be made of plastic. The compartment's number and size may vary widely as a function of the number of prescribed drugs and the duration of treatment.

Illustratively, the volume of the assembly may be 2 cm$^3$.

Moreover, a single-use disposable dispenser may be considered. However, the dispenser may also be re-used after taking it to the pharmacy for refilling and further treatment.

In one variation of the invention, the compartmentalized drawer constituting the pack 2 is covered by a hermetically sealed plastic foil 7 which may be transparent on the top.

In one particular embodiment, the compartmentalized drawer lacks a bottom, the plastic foil 7 enclosing it forms the upper and lower protecting and closing walls lending itself to be ruptured by local tear-off means 8 at the time of drug administration.

In another embodiment, the compartment's bottom (or possibly their upper and lower parts), includes a door driven by an opening device, thereby releasing the drugs through the bottom, the door resuming its initial position following drug release.

The dispenser 4 includes a container of a shape matching the pack 2 that acts as a drawer, so that once filled with predetermined drug doses and clad in the protecting foil 7, the drawer can slide in the foil. The container 4 is fitted, at least on its top or bottom surface, with as many apertures 9 as there are compartments in the pack 2. The apertures are configured opposite the compartments to allow removing a prescribed drug dose from a given compartment 6 by tearing open the protective film 7, which is opposite both the particular aperture 9 of the container 4, and the corresponding compartment 6.

In another variation, the dispenser 4 may be fitted at its lower part with an omitted recovery/dispensing element, whose purpose is to pick-up the doses issuing from the compartments and pass them easily to the patient. This recovery/dispensing element may have either an automatically, or a manually unlocking door.

The dispenser 4 includes a front door which may be fitted with a key for locking once the pack 2 is inserted.

In a preferred embodiment of the invention, the tear-open means 8 of the protective foil 7 of the container forming the dispenser 4 has either manually, or automatically operated doors situated in the apertures 9 of the container 4 and hinging on one of the aperture's sides so that, if being selectively forced inward, these doors will tear the upper and/or lower surfaces of the foil 7 enclosing the compartments 6 of the drawer 2, thereby releasing the drug dose held within a given compartment 6.

By means of a preset computer program, the dispenser's 4 doors 8 can be locked and unlocked in a selected sequence and as a function of the preset time intervals recorded in the storage substrate 3 and managed by an electronic clock.

With regards to dispenser 4, fitted with lower and upper doors, the lower and upper doors of a given compartment may be linked mechanically.

In another embodiment of the invention, the doors 8 are fitted with a means automatically returning them to their initial positions, thus locking them shut.

Moreover, a design may be adopted wherein a single control button drives all the doors 8, only one, namely the desired one, then being opened to release the drugs. Again there might be one button per door and only the door's particular button being able to drive it.

The computer program also includes selecting a unique individual.

The computer program may include an error detector to block the dispenser 4.

In another embodiment of the invention, an acoustic, and/or light and/or radio signal is emitted to notify a patient or remote medical personnel that an error took place, or of omission of drug administration.

FIG. 1 shows a second chart of both the method of the invention and its means of implementation.

This FIG. 1 shows a sub-assembly of the pack 2 and dispenser 4, with the doors 8 pivoting inside the compartments 6 and being denoted by switches 10.

The positions of the switches 10 indicate whether a door 8 is open or shut; the switches may be radio controlled using a preset program.

At the end of the time-window within which the drug should be taken, the invention's system is able to tell whether the corresponding door was opened. Detection is implemented by the processing unit 11 based on the data recorded in the storage substrate 3, with on door-position data, provided by the switches 10, and with real time provided by an internal clock, illustratively a component of the processing unit 11. If the door does not open, the alarm generator 17 generates an alarm which is transmitted through a transmission circuit 18 and a radio link to a nerve center 19, for instance of an apartment. The nerve center then calls an external agent, who subsequently contacts the patient. The external agent can communicate such omission by phone, or any other means, to the patient or may even intervene remotely to unlock by transmitted radio data 20 those doors that should have been opened, thus enabling the patient to access the drug. The system of the invention might allow other operational sequences such as automatic unlocking following a given time interval. However, priority is given to reliable drug administration, and to monitoring administration by an external agent. Moreover, prior to transmitting such an alarm signal, the processing unit 11 may transmit a control signal to a generator 13 which in turn may generate an alarm signal to a transducer which, depending on circumstance, may be visual or auditory. The alarm signal's purpose is to notify the patient, so that he or she may make good on the omission.

The patient may also personally trigger the alarm generator 17 by pushing a control button 15 driving the circuit 16. This option allows the patient to alert the external agent for telephone contact or any other subsequent action.

The support device described above may be composed of discrete or modular components, however, in its preferred embodiment, it is based on an appropriately programmed microprocessor.

The above, home-use system, operates as follows:

the medical personnel, or the user personally, if adequate for the task, inserts the pack 2 into the dispenser 4 and closes the front door, possibly using a key; in this manner each compartment 6 is situated opposite a door 8 which can be opened with a finger. However, the opening is monitored by the recorded program in the manner discussed above.

Following the insertion, the parameter-recording substrate 3 is read by the dispenser and the user's coordinates are checked. If an error is found, an acoustic message, is heard and the system is locked. In the case of the radio link option, a message, demanding a check, is transmitted to the base.

the data synthesized in the substrate 3 is processed means 5 reading the parameters of the storage substrate of the protected dispenser 4.

The system operates in the following manner:

when the pack 2 is inserted into the dispenser 4, all doors 8 of the compartments 6 are closed, the drug-taking schedule for each administration period lists the number of the compartment containing the drugs to be taken during this period (for instance the drug contained in compartment X must be taken between 11 AM and 1 PM), for each period of administration, an acoustic signal is emitted to alert the user to take the drug. Regarding the radio link embodiment, this signal is relayed to the external alarm site. Moreover, the closure of the door 8 corresponding to the designated compartment is impeded and therefore this door may be opened, and a visual display is activated (for instance a light on the front of the door will blink), the patient is able to press the door 8, rupturing the protective foil 7, and/or the bottom door of the compartments is actuated, and the drugs drop into the patient's other hand ready to be ingested, the top door (also any bottom door) is the pushed back, automatically returning to its initial position, for instance by means of a spring, closure is reactivated, and the door 8 then locked, all doors are closed between the scheduled times of drug administration, and as a result, the drugs are well protected against erroneous handling; during a time interval for ingestion, the only door that may be open, relates to the appropriate drug dosage; in this manner individuals with poor vision can proceed tentatively and still avoid errors, a person forgetting to take the drug within the ingestion time window, ordinarily can not open the door to the drug; if not critical, the ingestion time window may be as wide as desired, with regard to the radio link embodiment, and as required, a competent external agent may reopen the door remotely, possibly following discussion with the particular patient, the empty packs 2 can be removed and returned to the pharmacy.

In another embodiment of the invention, the system determines whether the patients are taking their drugs. In simple systems, that is without a radio link, such detection is feasible when the container is removed/replaced by competent personnel. With regards to the radio link option, statistics are kept in real time and intervention may take place as needed (emergency calls etc). This feature is significant for the pharmaceutical industry or research, where it is important to know the impact drugs have on patients' behavior and therapy. In this regard, the linkage to other monitoring devices is valuable, allowing evaluation of cause and effect directly and in real time.

One system of the invention also allows rationing drug supplies in the sense that they are supplied in precise amounts (accurate drug dosages) and, in the case of expensive drugs, to recover those not used. Recovery of costly drugs not taken by patients is an option because packaging by the method and device of the invention assures drugs remain clean and in good condition. Indeed, drug wastage is a large factor in the current increase of health costs.

What is claimed is:

1. A device supporting the administration of prescription drugs and free of patient intervention, wherein it comprises:

a pack receiving from the pharmacist at least one drug dose prepared beforehand by said pharmacist upon a physician's prescription, the pack then being sealed hermetically in order to be transmitted to the patient or to medical personnel, the pack consisting of a container divided into a plurality of compartments each of which receives beforehand at least one tablet corresponding to taking the given drugs to be ingested by the patient at a given dosage, a given time and at a given time interval, a storage substrate linked to the pack and bearing all the patient's identifying parameters, and the preparation relating to the prescribed drug, name of drugs, drug dosages, schedule of administration, a programmed dispenser which initially is locked and can be automatically or manually unlocked to dispense one or more drug doses as a function of the parameters stored in the storage substrate of the pack, means identifying and reading said parameters related to the dispenser and activated when said dispenser cooperates with the pack containing the drug doses to be administered, wherein the container constituting the pack is a compartmentalized drawer of overall parallelipipedic shape.

2. Device as claimed in claim 1, wherein the compartmentalized drawer constituting the pack is covered by a hermetically sealed plastic foil which is transparent at least at the top.

3. Device as claimed in claim 1, wherein the compartmentalized drawer lacks a bottom, while the plastic film includes local tear-off means and totally encloses the drawer so as to constitute the upper and lower closing and protective walls which can be destroyed using the local tear-off means at the time of drug administration.

4. A device supporting the administration of prescription drugs and free of patient intervention, wherein it comprises:

a pack receiving from the pharmacist at least one drug dose prepared beforehand by said pharmacist upon a physician's prescription, the pack then being sealed hermetically in order to be transmitted to the patient or to medical personnel, the pack having compartments, a storage substrate linked to the pack and bearing all the patient's identifying parameters, i.e. name, address, social security number etc. and the preparation relating to the prescribed drug: name of drugs, drug dosages, schedule of administration etc., a programmed dispenser which initially is locked and can be automatically or manually unlocked to dispense one or more drug doses as a function of the parameters stored in the storage substrate of the pack, means identifying and reading said parameters related to the dispenser and activated when said dispenser cooperates with the pack containing the drug doses to be administered, wherein the dispenser consists of a container having a shape corresponding to that of the pack constituting a drawer in such manner as to allow housing the drawer by sliding it once it has been filled with a predetermined drug dose and enclosed by a protective film, the container comprising at least at its upper or lower surfaces apertures and having as many apertures as there are compartments in the drawer-pack, the apertures being present opposite the compartments so as to allow removing from a given compartment a drug dose to be taken, namely by tearing open the protective foil which is situated opposite both the given aperture of the container and a corresponding cell.

5. Device as claimed in claim 3, wherein the container includes apertures and the tear-off means of the protective foil of the container constituting the dispenser consist of manually or automatically driven doors situated in the apertures of the container and hinging relative to the sides of the apertures in such manner that, by selectively pushing them inward, they shall cause tearing in the upper and lower surfaces of the foil enclosing the compartments of the drawer, thereby releasing the drug dose contained in a given compartment.

6. Device as claimed in claim 5, further comprising an electronic clock wherein the doors of the dispenser mechanically inter-connected and are driven by a preset and remote-controlled computer program to assure locking and unlocking the doors in a selected sequence and as a function of the preset time intervals managed by the electronic clock.

7. Device as claimed in claim 6, wherein the doors are fitted with means automatically returning them into their initial positions in order to resume closure entailing inaccessibility.

8. Device as claimed in claim 6, wherein the computer program comprises a function detecting a unique user.

9. Device as claimed in claim 6, wherein the computer program comprises an error-detecting function able to block the dispenser.

10. Device as claimed in claim 6, wherein the computer program comprises an unlocking function for a predetermined time T of one of the doors of the dispenser and corresponding to a compartment holding the dose to be ingested at that time T, the other compartments remaining locked.

11. Device as claimed in claim 6, wherein an acoustic and/or luminescent and/or radio signal shall be emitted to draw the attention of the patient or of the medical personnel remote from the premises in case of error or in case of forgetting drug administration.

* * * * *